US011085856B2

(12) United States Patent
Lopez Ferrer et al.

(10) Patent No.: US 11,085,856 B2
(45) Date of Patent: Aug. 10, 2021

(54) METHOD AND PRODUCT FOR PREPARING A PROTEIN-CONTAINING SAMPLE FOR ANALYSIS BY MASS SPECTROMETRY

(71) Applicant: Thermo Finnigan LLC, San Jose, CA (US)

(72) Inventors: Daniel Lopez Ferrer, San Carlos, CA (US); Aaron M. Robitaille, Seattle, WA (US); Michael O. Krawitzky, Santa Clara, CA (US); Greg A. Foster, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 5 days.

(21) Appl. No.: 15/705,526

(22) Filed: Sep. 15, 2017

(65) Prior Publication Data

US 2019/0086306 A1 Mar. 21, 2019

(51) Int. Cl.
*G01N 1/40* (2006.01)
*G01N 33/68* (2006.01)

(52) U.S. Cl.
CPC ....... *G01N 1/4044* (2013.01); *G01N 33/6848* (2013.01)

(58) Field of Classification Search
CPC ......................... G01N 1/4044; G01N 33/6848
See application file for complete search history.

(56) References Cited

U.S. PATENT DOCUMENTS

| | | | |
|---|---|---|---|
| 2007/0275478 | A1 | 11/2007 | Taranenko et al. |
| 2011/0195430 | A1 | 8/2011 | Lopez-Ferrer |
| 2014/0017716 | A1 | 1/2014 | Anderson |
| 2015/0140589 | A1 | 5/2015 | Meyer et al. |
| 2015/0361415 | A1 | 12/2015 | Meyer et al. |
| 2016/0341704 | A1 | 11/2016 | Meyer et al. |

FOREIGN PATENT DOCUMENTS

WO 2015/033479 A1 3/2015

OTHER PUBLICATIONS

Lopez-Ferrer et al., Anal. Chem., 2009, vol. 81, No. 15, p. 6272-6277.*

Lopez-Ferrer et al., Journal of Proteome Research, 2005, vol. 4, No. 5, p. 1569-1574.*

Pressure Unit Convertor via Google, retrieved on Jul. 30, 2019, 1 page.*

Biognosys, "Sample Preparation Kit—For reproducible mass spectrometry proteomics", Manual, 2017, pp. 1-11.

EMD Chemicals, "ProteoExtract® Subcellular Proteome Extraction Kit" in "Calbiochem® & Novagen®—Protein Sample Preparation Tools for Signal Transduction Research & Proteomics", 2007, pp. 1-16.

Expedeon, "FASP™ Protein Digestion Kit", Use and Storage Instructions, 2012, pp. 1-3.

Promega, "Rapid Digestion—Trypsin and Rapid Digestion—Trypsin/Lys-C Kits", Technical Manual, https://www.promega.com/-/media/files/resources/protocols/technical-manuals/500/rapid-digestion-trypsin-and-rapid-digestion-trypsin-lysc-kits-protocol.pdf, 2017, pp. 1-12.

Protifi, "S-Trap—Rapid universal MS sample prep", http://www.protifi.com/s-trap/, downloaded Sep. 26, 2017, pp. 1-2.

Thermo Scientific, "Fast Digestion Method Optimization Using Innovative Trypsin Technology", SMART Digest, App Note 21504, https://tools.thermofisher.com/content/sfs/brochures/AN-21504-SP-SMART-Digest-Digestion-Endpoint-AN21504-EN.pdf, 2016, pp. 1-4.

Waters, "Waters Application Notes—ProteinWorks", http://www.waters.com/webassets/cms/library/docs/720005583en.pdf, (2016), pp. 1-52.

* cited by examiner

*Primary Examiner* — Kade Ariani

(57) ABSTRACT

A method for preparing a protein-containing sample for analysis by mass spectrometry includes introducing the sample into a reaction vessel. The reaction vessel contains a reagent mixture including pre-measured quantities of an immobilized proteolytic enzyme, a reducing agent and an alkylating agent. The contents of the reaction vessel are activated by heating or by sonication.

11 Claims, 10 Drawing Sheets

Classic Method

- Cell Lysis
  5 min
- Protein Abundance
  30 min
- Denature Reduce Alkylate
  2 hours
- Lys-C/Trypsin Digestion
  4-18 hours

Promega New Kit

- Cell Lysis
  5 min
- Protein Abundance
  30 min
- Denature Reduce Alkylate
  2 hours
- Lys-C/Trypsin Digestion
  1 hour

PreOmics Kit

- Cell Lysis, Denature Reduce Alkylate
  10 min
- Lys-C/Trypsin Digestion
  1-3 hour

New Protocol

- Cell lysis Denature Reduce Alkylate Digestion
  5-90 min

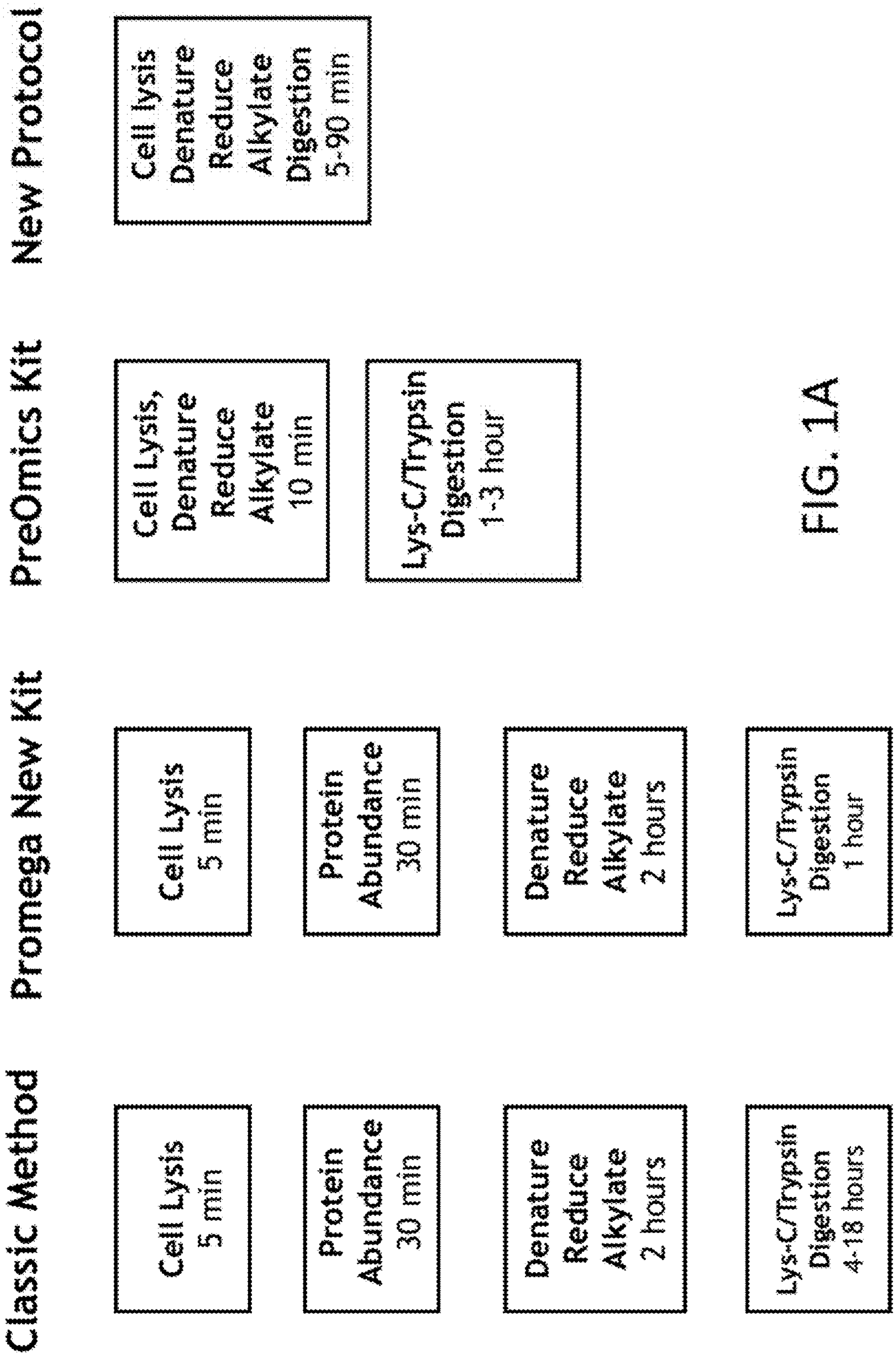

FIG. 1A

METHOD AND PRODUCT FOR PREPARING A PROTEIN-CONTAINING SAMPLE FOR ANALYSIS BY MASS SPECTROMETRY

FIELD OF THE INVENTION

This disclosure relates generally to biological sample preparation for subsequent mass spectrometric analysis. More particularly, this disclosure relates to a method and product for rapid proteolytic digestion of a protein-containing sample for analysis by mass spectrometry.

BACKGROUND

Mass spectrometry has emerged as the preferred method for in-depth characterization of the protein components of biological systems. Assuming that the biological sample is prepared properly, mass spectrometers are capable of elucidating amino acid sequences and identifying post-translational modifications, which are critical measurements in the determination of protein function and activity.

Current proteomic sample preparation methods consist of some or all of the following steps: cell lysis, protein reduction, alkylation, and digestion. The different steps are performed sequentially, requiring significant user involvement and long waiting times, which translates into a lack of reproducibility, and which is the cause of one of the major inconveniences for proteomic scientists. In fact, sample preparation is the major bottleneck in high throughput mass spectrometric proteomic studies.

Several kits are commercially available for use in preparing proteomic samples for subsequent analysis by mass spectrometry. In US 2014/0017716 A1, Anderson describes a proteolytic digestion kit with dried reagents, and a digestion protocol involving six reagent additions with a total processing time of more than sixteen hours. On the other hand, so-called rapid digestion kits, which reduce the processing time to between about one hour and about three-and-a-half hours, still involve multiple reagent additions, which may require significant user involvement and lead to user inconvenience.

It would therefore be beneficial to provide methods and products that overcome at least some of the above-mentioned disadvantages and/or limitations.

SUMMARY OF THE INVENTION

In accordance with an aspect of at least one embodiment there is provided a method for preparing a protein-containing sample for analysis by mass spectrometry, comprising: introducing the sample into a reaction vessel in which a reagent mixture is disposed, the reagent mixture including pre-measured quantities of an immobilized proteolytic enzyme, a reducing agent and an alkylating agent; and activating the contents of the reaction vessel.

In accordance with an aspect of at least one embodiment there is provided a method for manufacturing a product for use in preparing a protein-containing sample, comprising: providing a closeable reaction vessel having an internal volume; introducing a mixture comprising a predetermined amount of each of the following reagents into the internal volume of the closeable reaction vessel: an immobilized proteolytic enzyme; a reducing agent; and an alkylating agent.

In accordance with an aspect of at least one embodiment there is provided a product for use in preparing a protein-containing sample for mass spectrometry analysis, comprising: a closeable reaction vessel having an internal volume; and a reagent mixture disposed within the internal volume of the closeable reaction vessel and comprising a predetermined amount of each of the following: an immobilized proteolytic enzyme; a reducing agent; and an alkylating agent.

In accordance with an aspect of at least one embodiment there is provided a method for preparing a protein-containing sample for mass spectrometry analysis, comprising: concurrently reacting the sample with an alkylating agent, a reducing agent and an immobilized proteolytic enzyme; and activating the sample by performing at least one of heating the sample, sonicating the sample, and applying pressure to the sample.

BRIEF DESCRIPTION OF THE DRAWINGS

The instant invention will now be described by way of example only, and with reference to the attached drawings, wherein similar reference numerals denote similar elements throughout the several views, and in which:

FIG. 1A compares three prior art methodologies to a new protocol according to an embodiment.

DETAILED DESCRIPTION OF EMBODIMENTS OF THE INVENTION

Figure 1B:
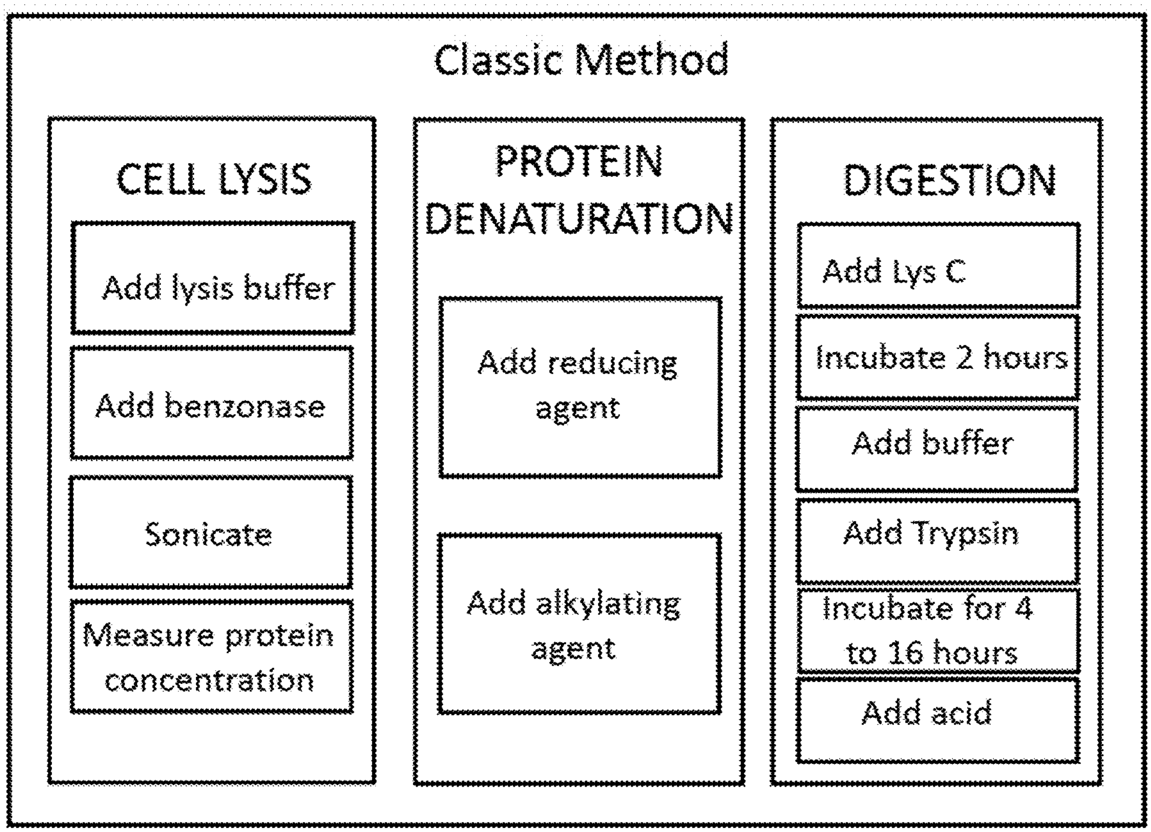
FIG. 1B depicts the workflow of the "classic method."

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

The term "alkylating efficiency" is defined as the quantitative relation between the number of detected cysteines that have been modified by the alkylating agent during the reaction and the total number of cysteines detected in the sample, as determined by analyzing the sample using mass spectrometry followed by a database search. A specific and non-limiting example includes alkylation of cysteine with chloroacetamide (CAA) or Iodacetic acid (IAC) that increases the mass of the peptide by 57.021 or 58.005 Daltons, respectively. This increase in mass is measured using a mass spectrometer and quantified during the database search.

The term "digestion efficiency" is defined as how much protein is partially digested or undigested. Usually, there are two key parameters to define the digestion efficiency, the enzyme specificity and number of missed cleavages. A specific and non-limiting example includes the following; trypsin cleaves peptide chains at the carboxyl side of arginine (R) or lysine (K) amino acids. If there are peptides that have an amino acid in their C-termini that is neither K nor R, those are considered semitryptic peptides. In the same way, looking at the protein sequence where the peptide comes from, if the amino acid before the n-terminal of the peptide is not K or R, it will be also considered a semitryptic peptide. In the case, that the previous examples occur at the same time we will have a non-tryptic peptide. In an optimal digestion for a proteomic experiment, the percentage of semitryptic or non-tryptic peptides is below 5%. The second key parameter is the number of missed cleavages, a missed cleavage occurs when trypsin fails to cleave a peptide at these residues, the peptide is considered to have a missed cleavage. If trypsin cleaves the peptide after all amino acids of arginine (R) or lysine (K), the peptide is considered fully digested. The number of peptides containing missed cleavages is kept below 10% in an optimal proteomic experiment.

The term "% of peptides" is defined as the quantitative relation between the number of peptides identified in the sample that have a specific characteristic and those that do not have the specific characteristic. This relationship is usually given in percentual units. The term "protein groups" is used as a quantitative measure of how many proteins have been identified in a given sample in a given proteomic experiment. The term group is used for those cases where a several proteins (e.g., Protein A, Protein B and Protein C) that have a high amino acid sequence homology, and the peptides identified during proteomic analysis have an amino acid sequence that it is shared among all the proteins, so that it is not possible to say whether the protein in the sample is A, B or C. Under these circumstances, the three proteins (in this example) are treated as a group.

Referring now to FIG. 1A, shown is an overview of the workflows of three prior art methodologies for preparing a protein-containing sample for subsequent analysis by mass spectrometry, as well as the workflow of a new one-step protocol according to an embodiment. The so-called "classic method" includes the steps of cell lysis, protein abundance determination, denaturation/reduction/alkylation, and digestion, all of which are performed sequentially. In the cell lysis step a lysis buffer solution, containing salts such as Tris-HCl or EDTA and optionally detergents such as Triton X-100 or SDS, is added to the sample to break open the cells contained therein. The "protein abundance" step provides a quantitative measure of protein in the sample, so that the concentration of trypsin used for the subsequent digestion step may be adjusted to yield a trypsin-to-protein ratio of about 1:50 (wt:wt). The proteins are then denatured with strong chaotropic agents such as urea or thiourea. This step is either followed by or combined with disulfide reduction using a reducing agent such as tris(2-carboxyethyl) phosphine (TCEP) or dithiothreitol (DTT). The free sulfhydryl groups on the cysteine residues are then alkylated with reagents such as iodoacetamide or iodoacetic acid to irreversibly prevent the free sulfhydryls from reforming disulfide bonds. The denatured, reduced and alkylated proteins are then digested by endoproteinases, (e.g., trypsin, chymotrypsin, Glu-C and Lys-C), which hydrolytically break peptide bonds to fragment proteins into peptides. The last two steps of the classic method are particularly time-consuming, accounting for most of the six-and-a-half to twenty-and-a-half hours required to complete a sample preparation.

The new one-step protocol according to an embodiment combines the cell lysis, denaturation/reduction/alkylation, digestion steps and reduces the total sample preparation time to between about 5 minutes and about 90 minutes. Optionally, depending on the sample that is to be digested, a two-step protocol is used in which the sample is transferred into the reaction vessel after performance of a separate cell lysis step. As an example, the one-step protocol is suitable for a sample comprising cells, while the two-step protocol is more suitable for a whole tissue sample.

Referring now to FIG. 1B, the "Classic Method" workflow is shown in more detail. Each step that was discussed with reference to FIG. 1A comprises a series of sub-steps, each requiring various reagent additions and/or other user intervention. The cell lysis step includes the addition of a lysis buffer and the addition of benzoate, after which sonication occurs. The protein concentration in the resulting solution is then determined in a separate step. Next, a protein denaturation step is performed by adding a reducing agent and an alkylating agent. The duration of the protein denaturation step is about 2 hours. Finally, a digestion step is performed by adding Lys C, usually at a 1:100 enzyme:substrate ratio, and incubating for about 2 hours, after which a buffer is added and trypsin is added, in this case the enzyme:substrate ratio tend to vary from 1:10 up to 1:100, and the sample is incubated again for an additional 4 to 16 hours. After an acid addition step to stop the enzymatic activity, the sample is ready to be cleaned up and analyzed by mass spectrometry.

Figure 1C:
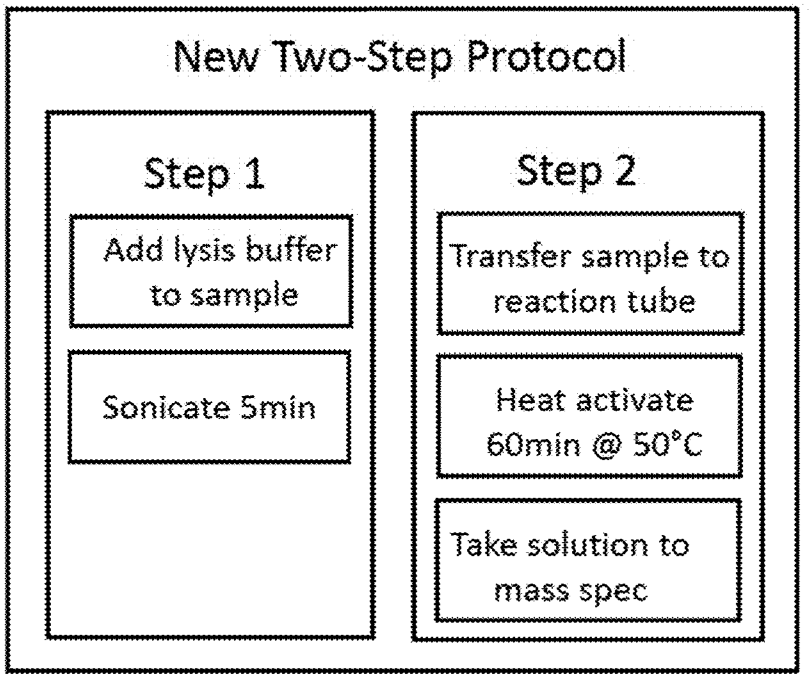
FIG. 1C depicts the workflow of a two-step protocol according to an embodiment.

Referring now to FIG. 1C, the two-step protocol according to an embodiment is shown in more detail. Samples that need an extra energy input during the protein extraction process are e.g., processed using the two-step protocol described below. In step 1 of the two-step protocol the sample is added to a sonication tube containing a lysis buffer. The lysis buffer contains a buffered solution, e.g. ammonium bicarbonate 50 mM pH 8.2 and suitable chaotropic agents or detergents that are capable of disrupting the hydrogen bonding network between water molecules and reducing the stability of the native state of proteins and membranes by weakening the hydrophobic effect. Usually, 6M urea, 1% SDS, 1% SDC are the typical additives. Once the lysis buffer has been added to the sample, the resulting solution is sonicated for e.g., about 5 minutes. High intensity ultrasound energy helps disrupt DNA as well as cell membranes, allowing proteins to be extracted efficiently from cellular matrices of the sample. In step 2 of the two-step method, the lysis buffer containing the sample is added to a reaction tube containing a reagent mixture including pre-measured quantities of immobilized proteolytic enzymes, a reducing agent, and an alkylating agent. By way of a specific and non-limiting example, 120 uL of immobilized trypsin slurry is added to the vessel, the beads are cleaned three times with ammonium bicarbonate, and then the supernatant is removed from the tube. A solution containing 5 mM of TCEP, 15 mM CAA in 50 mM ammonium bicarbonate pH 8.2 is then added to the beads and the mixture is ready for the sample to be added. Once the sample is added, the tube contents are heated at e.g., 50° C. for an additional e.g., 60 minutes. The tube or vessel can be centrifuged or the solution filtered out to remove the beads, after which the sample is ready to be analyzed by mass spectrometry.

Figure 1D:
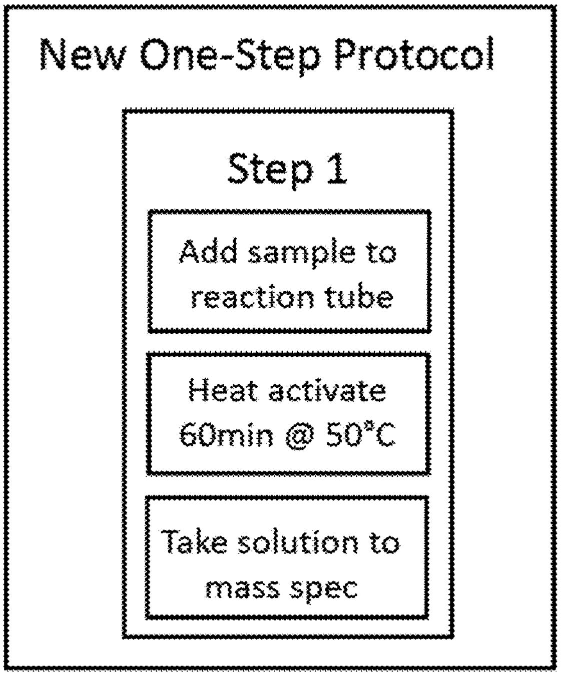
FIG. 1D depicts the workflow of a one-step protocol according to an embodiment.

Referring now to FIG. 1D, the one-step protocol according to an embodiment is shown in more detail. In step 1 of the one-step protocol the user adds the sample into a reaction vessel containing a reagent mixture including a lysis buffer, pre-measured quantities of an immobilized proteolytic enzyme, a reducing agent and an alkylating agent. The contents of the reaction vessel are then activated, such as for instance by sonication for a period of about 5 minutes or by heating between 37° C. and 50° C. for between five and ninety minutes. As used herein, the term "activating" and its cognates refers to the act of adding energy to the contents of the reacting vessel so as to accelerate the rate of the desired reaction of the sample (or components thereof) with the various reagents. This workflow is envisioned for use with, for instance, mammalian cells and other types of samples such as purified proteins where exhaustive protein extraction is not needed, and the ultrasound step can be skipped during the protein extraction step. In some implementations, activating can refer to applying a pressure of between 500 psi and 45 kpsi for ten minutes or less.

A specific and non-limiting example of the one-step protocol according to an embodiment uses a closeable reaction vessel, such as for instance an Eppendorf tube, which contains a reagent mixture prepared using 1 μL tris(2-carboxyethyl)phosphine (TCEP) 0.2 M solution, 0.2 mg of CCA, 0.8 mg of $CaCl_2$ and 50 μL Poroszyme® immobilized trypsin beads. In this example, the reagent mixture includes a proteolytic enzyme in the form of immobilized trypsin (such as Poroszyme® beads, available from Thermo Fisher Scientific), however, other suitable immobilized enzymes may be used, as long as the immobilization process helps to stabilize the secondary and tertiary structure of the protein without decreasing its activity. Importantly, having the enzyme immobilized to a solid support allows the enzyme to be present in a very high enzyme:substrate ratio (i.e. 100:1), forcing the enzyme kinetics to speed up due to its dependence on enzyme concentration. Advantageously, the immobilized enzyme does not contaminate the sample and it can easily be removed from the sample, since the solid support is very easy to separate from the solution. A non-limiting list of alternative reagents and/or concentrations includes at least the following: buffer pH: 7.8-8.2; reducing agent TCEP 1-5 mM; alkylating agent CAA 10 mM-25 mM; alkylating agent IAC 1-5 mM; alkylating agent IAA 1-15 mM; and $CaCl_2$ 0.1-1 mM. As suggested above, the reagent mixture optionally includes a proteolytic enzyme other than trypsin, such as for instance one of LysC, LysN, AspN, GluC, ArgC or chymotrypsin. Optionally, the reagent mixture is dried down and is stored below room temperature prior to use, such as for instance stored at 4° C., −20° C. or −80° C.

In certain embodiments of the invention, the reagent mixture contained within the prepared reaction vessel includes an isobaric labeling reagent that reacts with the peptides formed by protein digestion to produce isotopically labeled peptides. For example, a kit prepared in accordance with an embodiment may include a set of reaction vessels containing the above-described reagent mixture (comprising reducing and alkylating agents and immobilized proteolytic enzyme), each one of which further contains a different isotopologue of an isobaric labeling reagent, such that differentially labeled samples may be prepared and subsequently combined so as to determine relative quantities of peptides of interest via analysis by liquid chromatography-mass spectrometry, using techniques well known in the art. Isobaric labeling reagents are available from Thermo Fisher Scientific under the trade name Tandem Mass Tags.

Figures 12A, 12B:
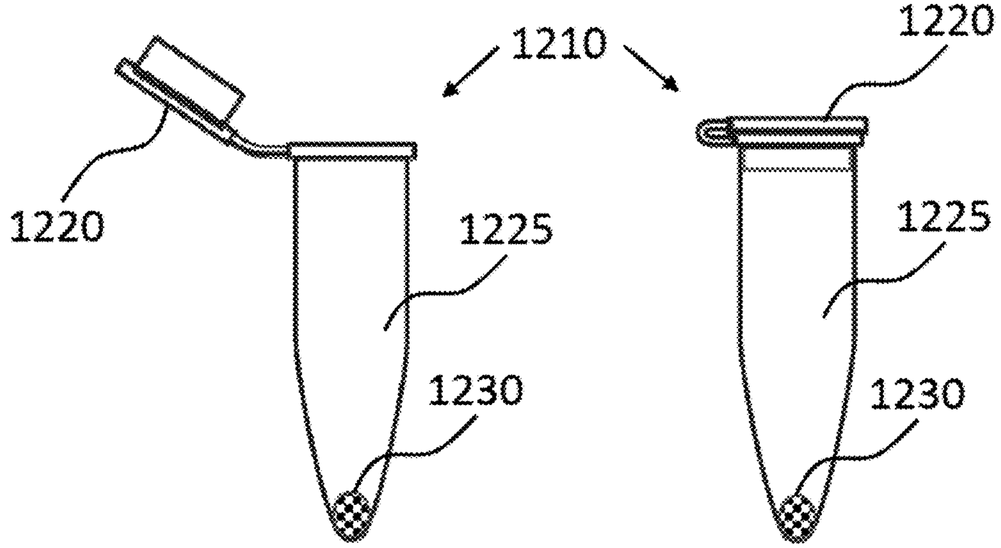
FIG. 12A depicts an example of a closeable reaction vessel in the form of an Eppendorf tube, which may be employed in connection with embodiments of the present invention, in an open condition and containing a reagent mixture.
FIG. 12B depicts the reaction vessel of FIG. 12A in a closed condition and containing a reagent mixture.

FIGS. 12A and 12B depict an example of a closeable reaction vessel 1210, which may be employed in connection with embodiments of the present invention, in an open and closed condition, respectively. Reaction vessel 1210 is provided with a lid 1220 that can be removed to allow the introduction of sample into the interior 1225 of the reaction vessel and then replaced to secure the contents within and avoid contamination. The reagent mixture 1230, disposed within vessel 1210, may be added to the reaction vessel during the product manufacturing process and may be dried to remove solvent. Vessel 1210 may be of any suitable type and geometry, such as the Eppendorf tube depicted in the drawing, and is preferably manufactured from materials that are inert with respect to the sample and reagents. The one-step protocol therefore includes resuspending a cell pellet or other suitable protein-containing sample in 150 μL of digestion buffer, and transferring the resulting sample into the reaction vessel that is charged with a mixture of reagents such as described in the previous paragraph. After the contents of the reaction vessel are activated, the supernatant is taken and cleaned up or injected into a LC-MS.

A series of experimentally determined results are presented in the following tables, and are discussed below with reference thereto. The results that are presented for the "current method" were all obtained using the one-step protocol, described supra.

TABLE 1

| Alkylation efficiency and digestion efficiency for different activation types. | | |
|---|---|---|
| Activation Type | Alkylation Efficiency | Digestion Efficiency |
| Classic Method (Heating 37° C.) | 100.0% | 95.8% |
| Current Method (Sonication) | 92.0% | 84.0% |
| Current Method (Heating 50° C.) | 98.4% | 88.1% |
| Current Method (Heating 60° C.) | 99.5% | 84.0% |

Table 1 presents experimental results that were obtained using the Classic Method (traditional protocol) and the method according to an embodiment of the invention with activation by sonication or heating at different temperatures. Here, the temperature of activation varied from 37° C. to 50° C. or utilized sonication, while all other variables for the method remained constant (alkylation reagent as CAA, etc.). As will be apparent, both the alkylation efficiency and the digestion efficiency are reduced, relative to the Classic method (100.0% and 95.8%, respectively), using the current method with activation by sonication (92.0% and 84.0%, respectively), heating at 50° C. (98.4% and 88.1%, respectively), and heating at 60° C. (99.5% and 84.0%, respectively). That said, the current method with activation by heating at 50° C. approximates the results that are achieved using the Classic Method, and acceptable results are also obtained using the other activation types.

TABLE 2

| Alkylation efficiency and digestion efficiency for different activation times. | | |
|---|---|---|
| Activation Time | Alkylation Efficiency | Digestion Efficiency |
| Classic Method (16 h) | 99.1% | 92.9% |
| Current Method (90 min) | 98.4% | 88.1% |
| Current Method (60 min) | 98.5% | 87.3% |
| Current Method (30 min) | 95.5% | 84.3% |

Table 2 presents experimental results obtained using the Classic Method (traditional protocol) and the method according to an embodiment of the invention with different activation durations of 30 min, 60 min or 90 min Only the activation duration was varied, while all other variables for the method according to an embodiment of the invention remained constant (temperature 50° C. and alkylation reagent as CAA, etc.). As will be apparent, both the alkylation efficiency and the digestion efficiency are reduced, relative to the Classic method (99.1.0% and 92.9%, respectively), using the current method with activation for 90 minutes (98.4% and 88.1%, respectively), for 60 minutes (98.5% and 87.3%, respectively), and for 30 minutes (99.5% and 84.3%, respectively). That said, the current method with activation by heating at 50° C. for at least 60 minutes approximates the results that are achieved using the Classic Method.

TABLE 3

| Alkylation efficiency and digestion efficiency using different reagents. | | |
|---|---|---|
| Alkylation Reagent | Alkylation Efficiency | Digestion Efficiency |
| Classic Method (with IAA alkylation reagent) | 98.9% | 92.8% |
| Current Method (with CAA alkylation reagent) | 98.1% | 90.1% |
| Current Method (with IAC alkylation reagent) | 99.2% | 93.4% |

Table 3 presents experimental results obtained using the Classic Method (traditional protocol) and the method according to an embodiment of the invention with different alkylation conditions. More particularly, IAA alkylation reagent was used for the Classic Method, and either CCA or IAC alkylation reagent was used for the method according to an embodiment of the invention but with all other variables for the method being the same (e.g., activation temperature 50° C. and activation duration of 60 min, etc.). As is apparent, the alkylation efficiency and the digestion efficiency achieved using the method according to an embodiment of the invention, with either CCA or IAC alkylation reagent, closely approximate the results that are achieved using the Classic Method.

TABLE 4

| Alkylation efficiency and digestion efficiency for different amounts of protein in the sample. | | |
|---|---|---|
| Amount of Protein | Alkylation Efficiency | Digestion Efficiency |
| 1000 µg | 98.2% | 90.0% |
| 800 µg | 95.5% | 91.1% |
| 600 µg | 95.4% | 91.5% |
| 400 µg | 93.2% | 91.2% |
| 200 µg | 97.6% | 92.3% |
| 100 µg | 97.2% | 92.1% |
| 50 µg | 98.7% | 92.3% |
| 25 µg | 100.0% | 93.2% |
| 10 µg | 100.0% | 94.0% |

Table 4 presents experimental results obtained using the method according to an embodiment of the invention, with different amounts of protein in the sample. Here the amount of protein digested varied from 10 ug to 1000 ug, while all other variables for the method remained constant (activation temperature 50° C., time of activation 60 min, alkylation reagent CAA, etc.) As will be apparent, both the alkylation efficiency and the digestion efficiency exceed 90% over the entire range of samples investigated.

Figure 2:
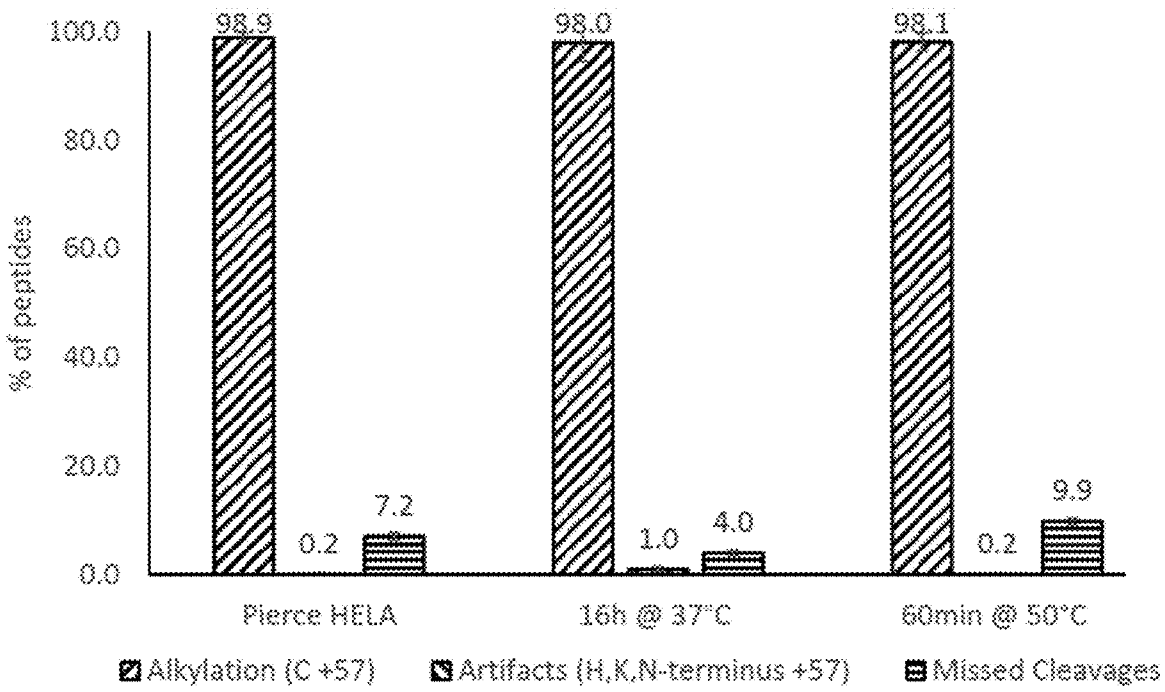
FIG. 2 is a bar graph showing the % of peptides obtained for one million HELA cells lysed using the Pierce HELA protocol, the "classic method" with heating for 16 h at 37° C., and the one-step protocol according to an embodiment with heating for 1 h at 50° C.
Figure 3:
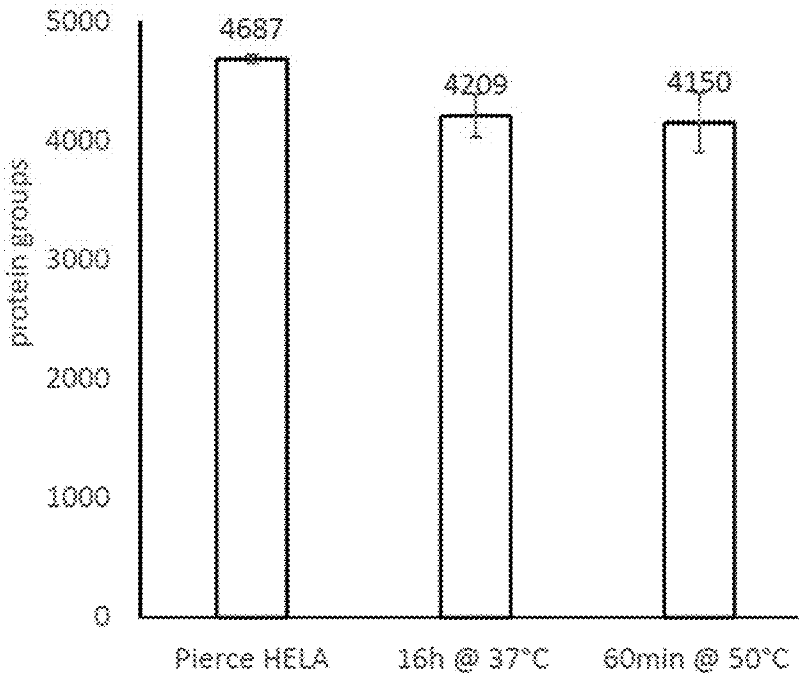
FIG. 3 is a bar graph showing the number of protein groups obtained for one million HELA cells lysed using the Pierce HELA protocol, the "classic method" with heating for 16 h at 37° C., and the one-step protocol according to an embodiment with heating for 1 h at 50° C.
Figure 4:
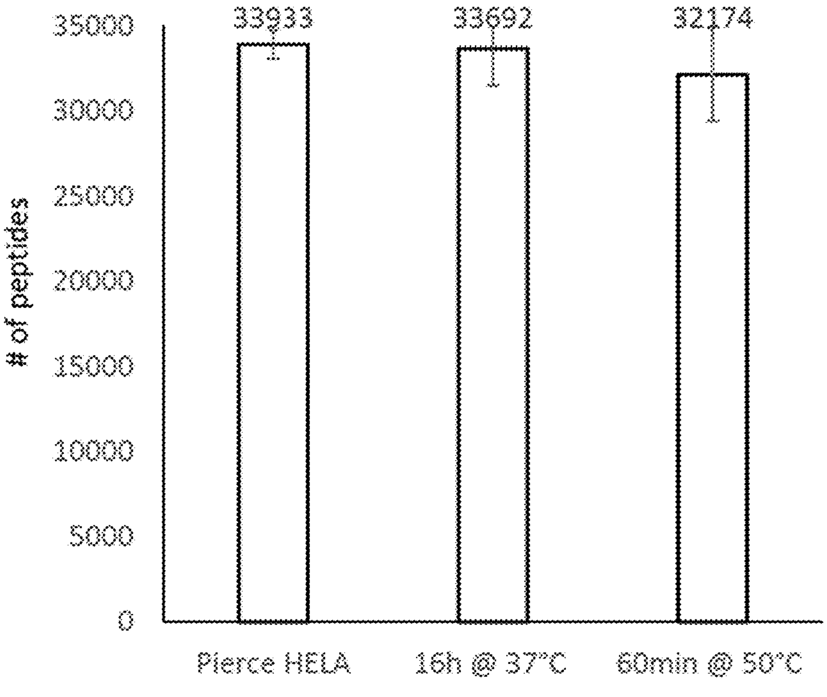
FIG. 4 is a bar graph showing the number of peptides obtained for one million HELA cells lysed using the Pierce HELA protocol, the "classic method" with heating for 16 h at 37° C., and the one-step protocol according to an embodiment with heating for 1 h at 50° C.

Referring now to FIGS. 2-4, shown are the experimentally determined values for "% peptides," "peptide groups," and "# of peptide," obtained for samples that were prepared using the new protocol according to an embodiment of the invention, or using traditional protocols (Pierce HELA and 16 h @37° C. are the traditional protocols). In each case, one million HELA cells were first disrupted and digested. After digestion, peptide concentration was measured and 1 µg of digested peptides were transferred to an autosampler vial, and then analyzed by LC-MS/MS using a 2 h gradient in a Thermo Scientific EASY-nLC1200 system coupled to a Thermo Scientific Q Exactive HF mass spectrometer. N=4 biological replicates. (Pierce HELA and 16 h @37° C. are the traditional protocols.)

FIG. 2 compares the chemical treatment of cysteines and the digestion efficiency for a commercial HELA digest standard ("Pierce HELA" Thermo Fisher Scientific, Rockford, Ill., USA) that is commonly used to evaluate LC-MS performance, the traditional method with heating for 16 hours at 37° C., and the new protocol according to an embodiment of the invention. The histogram compares the % of peptides modified by the treatment intentionally (i.e. alkylation of cysteines), unintentionally (artifacts at other amino acids due to unspecific reactions) and how specific the immobilized trypsin cleaves the proteins (missed cleavages) compared to the free trypsin used in the other methods.

FIG. 3 compares the overall performance of the three workflows, in particular plotting the number of protein groups identified in samples prepared using the same three methods, i.e., classic method Pierce HELA, classic method with heating for 16 h at 37° C., and new protocol with heating for 1 h at 50° C. The results are similar for each of the methods, however the new protocol achieves a large decrease in total time required—only about 1 h verses about 16 h for the classic method. Pierce HELA shows ~10% more protein groups, however since the number of peptides is very similar (see FIG. 4) the observed difference could be due to different cell culture or processing conditions that are inducing a small bias.

FIG. 4 compares the number of peptides obtained for classic method Pierce HELA, for classic method with heating for 16 h at 37° C., and for the new protocol according to an embodiment of the invention with heating for 1 h at 50° C. The number of protein groups is lower for both the classic method with heating for 16 h at 37° C. and for the new protocol with heating for 1 h at 50° C., compared to Pierce HELA. Although the number of peptides is lower for the new protocol with heating for 1 h at 50° C., compared to both the Pierce HELA and heating for 16 h at 37° C. traditional protocols, it is noteworthy that the total time required is reduced to only about one hour.

Considering FIGS. 2-4 collectively, it is concluded that the new protocol according to an embodiment of the invention with heating for 1 h at 50° C. provides results that compare favorably to the results that are obtained using the classic methods (Pierce HELA and 16 h @37° C.), but with a significantly reduced total processing time.

Figure 5:
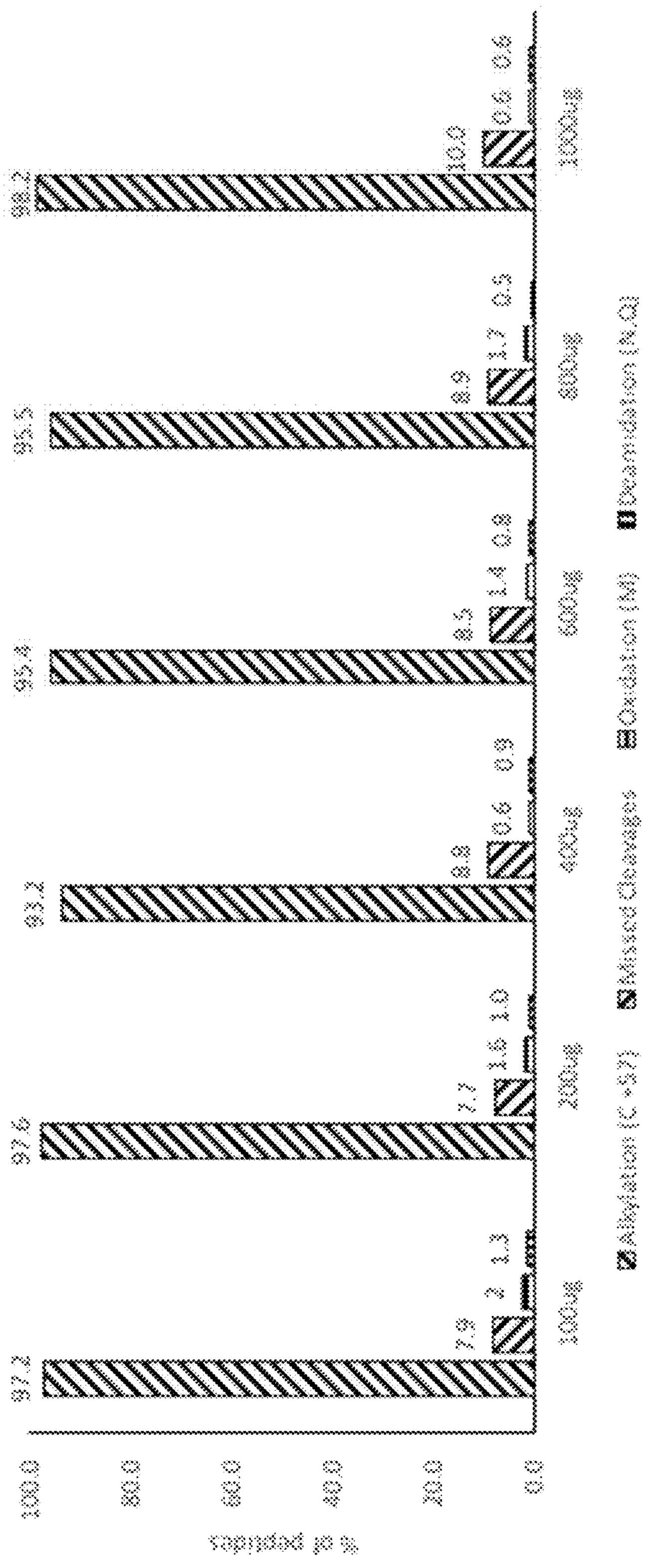
FIG. 5 is a bar graph showing the % of peptides obtained using the one-step protocol according to an embodiment, for samples containing the following amounts of protein: 100 μg, 200 μg, 400 μg, 600 μg, 800 μg and 1000 μg.
Figure 6:
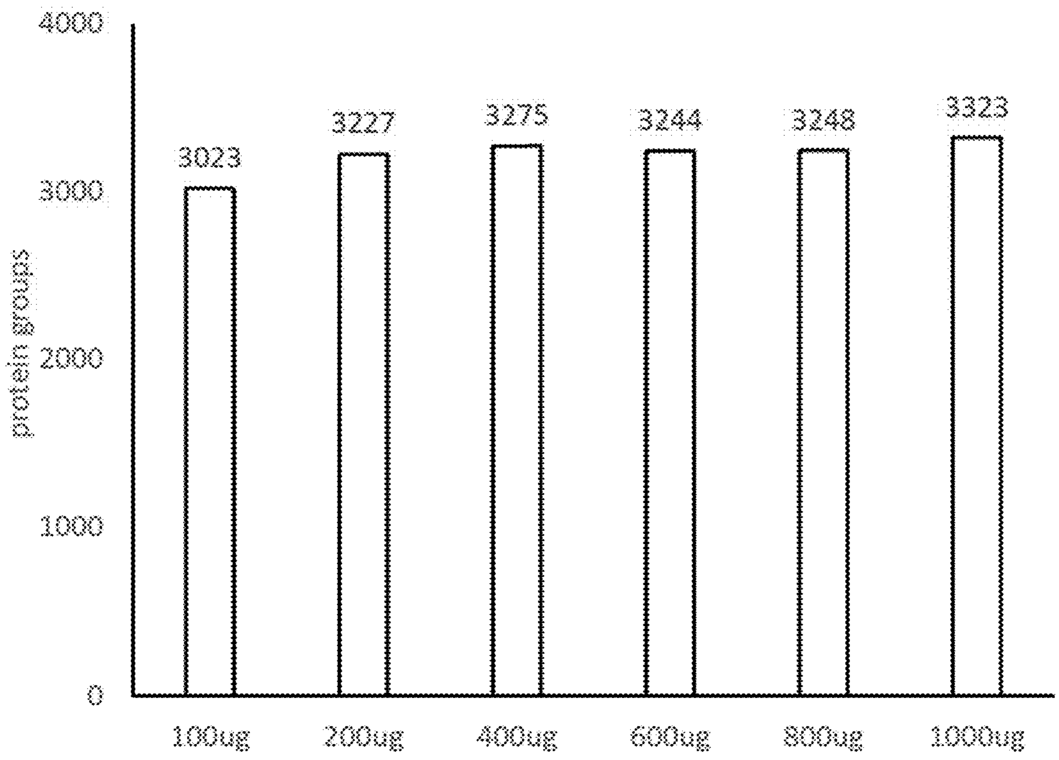
FIG. 6 is a bar graph showing the number of protein groups obtained using the one-step protocol according to an embodiment, for samples containing the following amounts of protein: 100 μg, 200 μg, 400 μg, 600 μg, 800 μg and 1000 μg.
Figure 7:
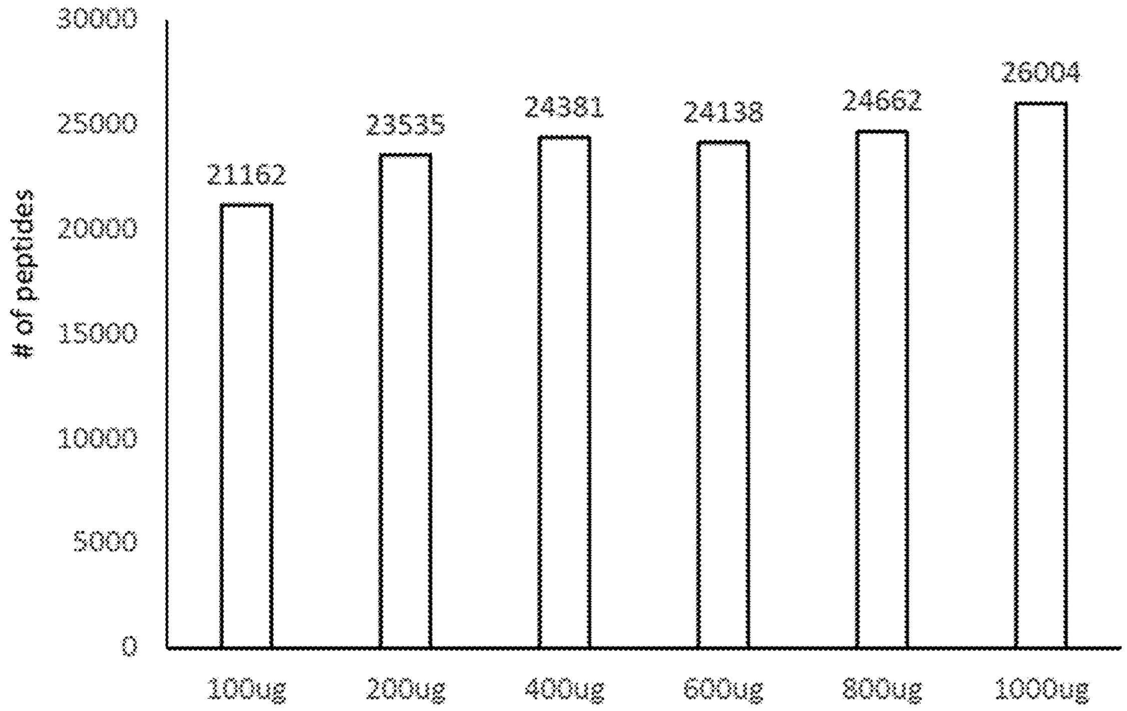
FIG. 7 is a bar graph showing the number of peptides obtained using the one-step protocol according to an embodiment, for samples containing the following amounts of protein: 100 μg, 200 μg, 400 μg, 600 μg, 800 μg and 1000 μg.

Referring now to FIGS. 5-7, shown are the experimentally determined values for "% peptides," "peptide groups," and "# of peptide," obtained for samples containing different weights of protein, and prepared using the new protocol according to an embodiment of the invention. An advantage of using an immobilized digestion enzyme is that the protocol is agnostic on the amount of protein in the sample that is being prepared. In fact, FIGS. 5-7 present the results that were obtained for a series of samples containing weights of protein spanning an order of magnitude. HELA cells were lysed in 150 μL of digestion buffer using heat (1 h at 50° C.). To determine the concentrate of protein over which the method could be utilized, proteins were quantified using UV, and a weight of protein between 100 ug-1000 ug was digested with 50 μL immobilized trypsin. After the digestion, 1 μg of digested peptides from each of the concentration points was analyzed on a 2 h gradient using a nanoLC-1200/QE-HF.

FIG. 5 compares the % of peptides obtained for samples that contain the following amounts of protein: 100 μg, 200 μg, 400 μg, 600 μg, 800 μg, and 1000 μg. As is apparent, based on the values that are presented in FIG. 5, the new protocol according to an embodiment of the invention provides very similar results over a wide range of protein concentrations. Further, the values shown in FIG. 5 are all similar to the values for the classic methods presented in FIG. 2.

FIG. 6 compares the protein groups that are obtained using the new protocol, from samples that contain the following amounts of protein: 100 μg, 200 μg, 400 μg, 600 μg, 800 μg and 1000 μg. The results that are presented in FIG. 6 further demonstrate that the new protocol works over a wide range of protein concentrations.

FIG. 7 compares the number of peptides obtained using the new protocol, from samples that contain the following amounts of protein: 100 μg, 200 μg, 400 μg, 600 μg, 800 μg, and 1000 μg. The results that are presented in FIG. 7 also further demonstrate that the new protocol works over a wide range of protein concentrations.

Figure 8:
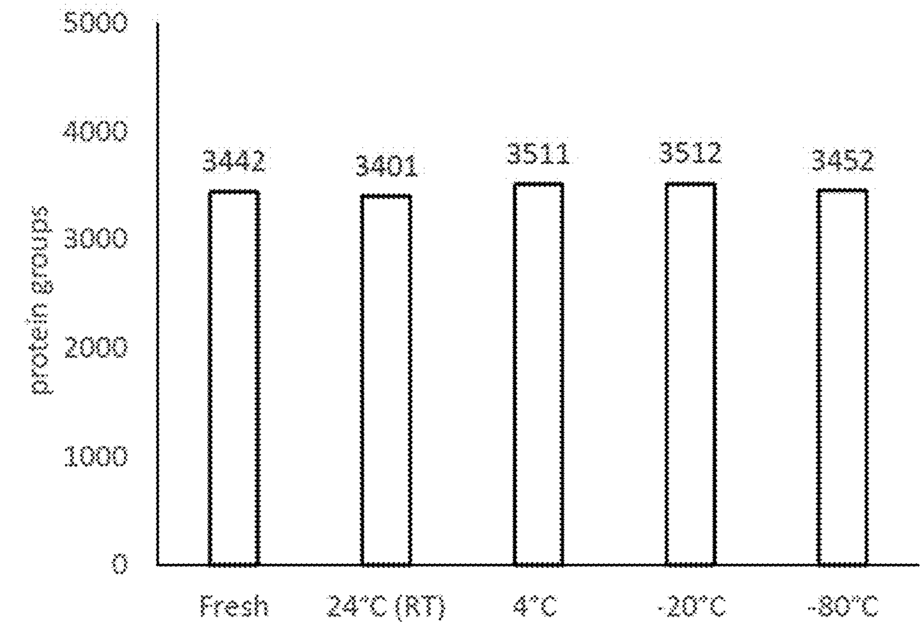
FIG. 8 is a bar graph showing the number of protein groups obtained for protein-containing samples prepared using fresh reagents, and for samples prepared using reagents that were stored for three weeks at 24° C., 4° C., −20° C. and −80° C.
Figure 9:
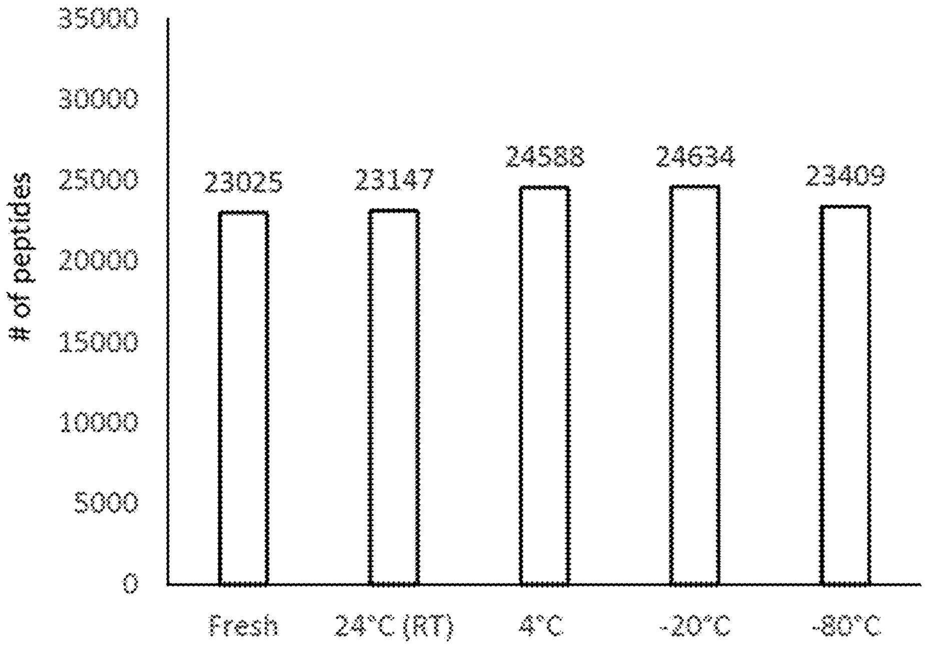
FIG. 9 is a bar graph showing the number of peptides obtained for protein-containing samples prepared using fresh reagents, and for samples prepared using reagents that were stored for three weeks at 24° C., 4° C., −20° C. and −80° C.
Figure 10:
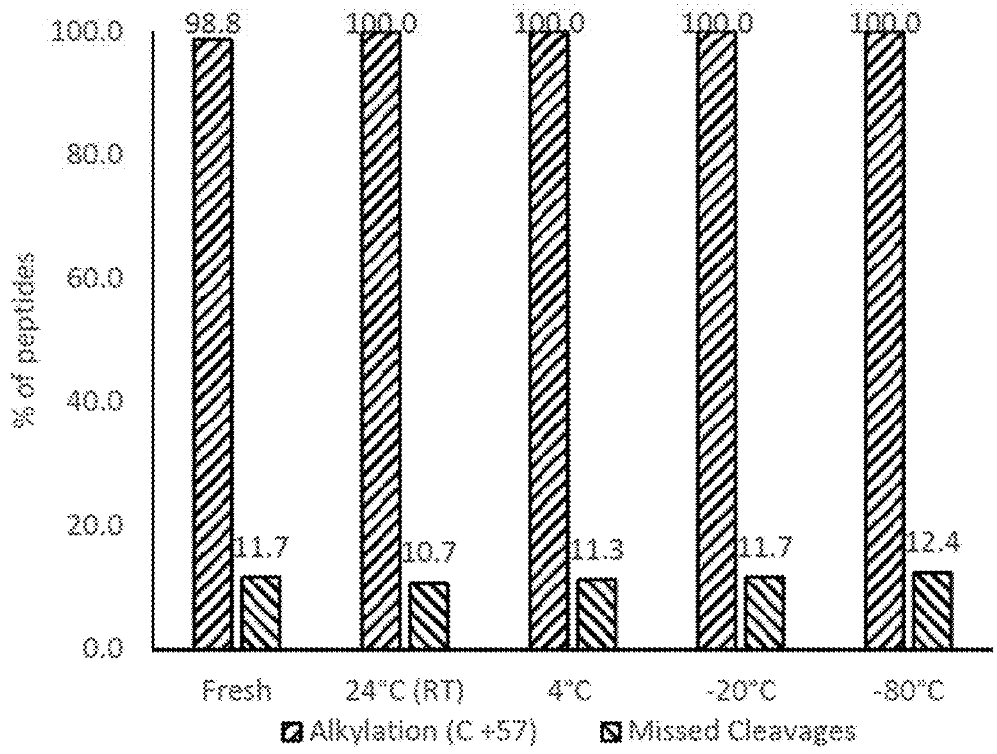
FIG. 10 is a bar graph showing the % of peptides obtained for protein-containing samples prepared using fresh reagents, and for samples prepared using reagents that were stored for three weeks at 24° C., 4° C., −20° C. and −80° C.

The stability of the reaction mixture that is employed in the new protocol, which includes immobilized trypsin, a reducing agent (TCEP), and an alkylating agent (CAA), was investigated and the results are presented in FIGS. 8-10. More particularly, the reagent mixture was prepared and then stored at various temperatures between −80° C. and 24° C. for a period of three weeks, prior to being used to incubate samples containing one million HELA cells. The HELA cells were added to previously stored reaction mixture, and digested using the new protocol according to an embodiment of the invention (i.e., with heating for 1 h @50° C.). After the digestion, 1 ug of digested peptides were transferred to an autosampler vial, and then analyzed by LC-MS/MS using a 2 h gradient in a Thermo Scientific EASY-nLC1200 system coupled to a Thermo Scientific Q Exactive HF mass spectrometer.

FIG. 8 compares the protein groups obtained using the new protocol, from samples that were prepared using fresh reagents and from samples that were prepared using reagents that were stored for three weeks at temperatures of 24° C., 4° C., −20° C. and −80° C. As is apparent, based on the values that are presented in FIG. 8, the reaction mixture that is used with the new protocol according to an embodiment of the invention remains stable after storage for three weeks at all temperature tested.

FIG. 9 compares the number of peptides obtained using the new protocol, from samples that were prepared using fresh reagents and from samples that were prepared using reagents that were stored for three weeks at temperatures of 24° C., 4° C., −20° C. and −80° C. The results that are presented in FIG. 9 further demonstrate that the reaction mixture remains stable after storage for three weeks at all temperature tested.

FIG. 10 compares the % of peptides obtained using the new protocol, from samples that were prepared using fresh reagents and from samples that were prepared using reagents that were stored for three weeks at temperatures of 24° C., 4° C., −20° C. and −80° C. The results that are presented in FIG. 10 also further demonstrate that the reaction mixture remains stable after storage for three weeks at all temperature tested.

Figure 11:
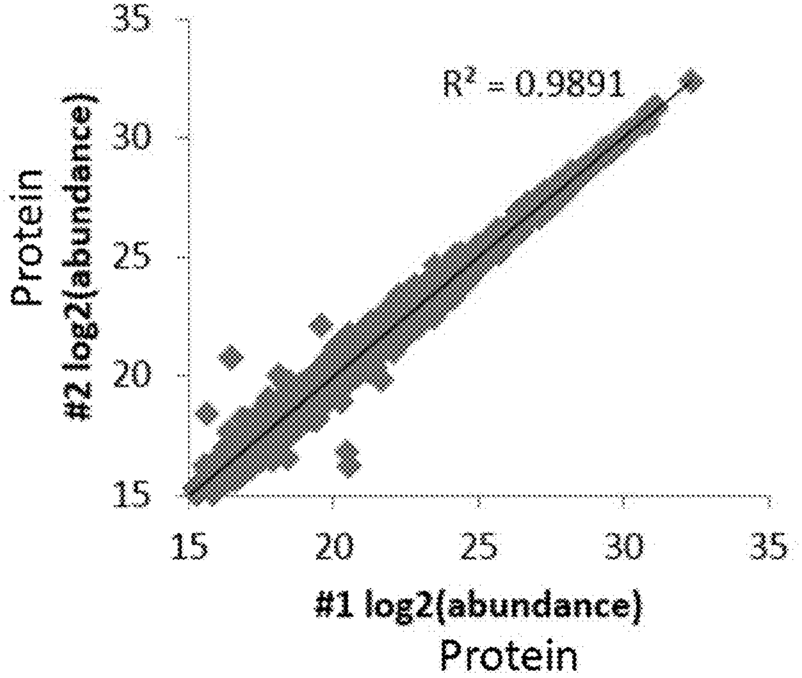
FIG. 11 is a scatter plot showing the protein abundance from two replicate samples prepared in the same manner.

For FIG. 11, one million HELA cells were analyzed using the new protocol according to an embodiment of the invention (n=2 biological replicates). 1 μg of digested peptides were analyzed on a 2 h gradient using a nanoLC-1200/QE-HF. Searches were done in PD 2.2 with LFQ quantitation. Protein abundance was then graphed on a scatter plot to determine reproducibility. The results that are presented in FIG. 11 demonstrate that the new protocol according to an embodiment of the invention yield reproducible protein quantification results.

The foregoing described embodiments are merely examples of devices according to the invention. It should be understood that various modifications may be made to the shown embodiments whilst still falling within the scope of the invention.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising"

and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A method for preparing a protein-containing sample for analysis by mass spectrometry, comprising:

introducing the sample into a reaction vessel in which a reagent mixture is disposed, the reagent mixture including pre-measured quantities of an immobilized proteolytic enzyme, a reducing agent and an alkylating agent, wherein the sample is a whole tissue sample; and activating the contents of the reaction vessel.

2. The method of claim 1, wherein the proteolytic enzyme is selected from the group consisting of trypsin, LysC, LysN, AspN, GluC, ArgC and chymotrypsin.

3. The method of claim 1, wherein activating comprises sonicating the contents of the reaction vessel for between 30 seconds and 30 minutes.

4. The method of claim 1, wherein activating comprises heating the contents of the reaction vessel at a temperature between 37° C. and 60° C. for between 5 minutes and 90 minutes.

5. The method of claim 1, wherein activating comprises applying a pressure of between 500 psi and 45 kpsi for ten minutes or less.

6. The method of claim 1, wherein the sample contains between 10 ng and 1000 pg of protein.

7. The method of claim 1, wherein the sample contains between 1 cell and 1 billion cells.

8. The method of claim 1, wherein the reagent mixture further includes a cell lysing agent.

9. The method of claim 8, wherein the cell lysing agent is selected from the group consisting of: a detergent in an amount between 0.01% and 5% (vol/vol), an organic solvent in a between 1% and 80% (vol/vol), and urea between 100 mM and 8M as calculated after sample is added.

10. The method of claim 1, wherein the sample is lysed prior to introducing into reaction vessel.

11. The method of claim 1, wherein activating the contents of the reaction vessel includes activating the sample and the reagent mixture including the immobilized proteolytic enzyme, the reducing agent, and the alkylating agent at a same time.

* * * * *